United States Patent [19]
Witt et al.

[11] Patent Number: 5,429,798
[45] Date of Patent: Jul. 4, 1995

[54] DEODORIZATION OF USED FOAM MOLDINGS, IN PARTICULAR FISH CRATES

[75] Inventors: Michael Witt, Ludwigshafen; Dietrich Scherzer, Neustadt; Klaus Hahn, Kirchheim; Rolf Henn, Ketsch; Wolf-Dieter Back, Neustadt, all of Germany

[73] Assignee: BASF Aktiengesellschaft, Ludwigshafen, Germany

[21] Appl. No.: 208,843

[22] Filed: Mar. 11, 1994

[30] Foreign Application Priority Data

Mar. 17, 1993 [DE] Germany ............... 43 08 430.3

[51] Int. Cl.⁶ .................................................. A61L 9/00
[52] U.S. Cl. ............................................. 422/5; 422/1
[58] Field of Search .......................... 422/1, 5, 26, 28

[56] References Cited

U.S. PATENT DOCUMENTS 3,113,104 12/1963 Bersworth ......................... 422/5

FOREIGN PATENT DOCUMENTS 252695 1/1988 European Pat. Off. .

OTHER PUBLICATIONS

Derwent Publications Ltd., AN 84–130968(21) (English abstract of JP-A 59 066 500, Apr. 14, 1984).
Derwent Publications Ltd., AN 92–145117(18) (English abstract of JP-A 4 077 534, Mar. 11, 1992).
Derwent Publications Ltd., AN 84–097722(16) (English abstract of JP-A 59 043 037, Mar. 9, 1984).
Derwent Publications Ltd., AN 90–012612(02) (English abstract of JP-A 1 293 872, Nov. 27, 1989).
Japanese Abstract, JP 62/194 863.
Japanese ABstract, JP 60/261 459.
Japanese Abstract, JP 63/59 962.
Japanese Abstrat, JP 54/28 826.
Kunststoffe 67 (1977) 10, 617–621.

*Primary Examiner*—Robert J. Warden
*Assistant Examiner*—Theresa T. Snider
*Attorney, Agent, or Firm*—Keil & Weinkauf

[57] ABSTRACT

A process for the deodorization of used foam moldings, in which the used foam moldings are treated
  a) with an aqueous solution of phosphoric acid, water-soluble primary or secondary phosphates or mixtures thereof.

3 Claims, No Drawings

DEODORIZATION OF USED FOAM MOLDINGS, IN PARTICULAR FISH CRATES

BACKGROUND OF THE INVENTION

1. Field of the Invention

The present invention relates to a process for the deodorization of used foam moldings, in particular fish crates.

Fish crates made from expandable polystyrene (EPS) cannot be recycled directly, since the typical fish odor (principally caused by trimethylamine) cannot be removed by thermal melting in conventional extruders. Many of the measures described in the literature for eliminating this odor problem have the disadvantage that the odor-forming impurities cannot actually be removed, but instead are merely bound or the unpleasant odor is merely covered by other odors.

2. Description of the Related Art

Mention should be made here, in particular, of iron salts in combination with various carboxylic acids (JP-A-62/194 863), colchicine (JP-A-60/261 459), cyclodextrin (JP-A-63/59 962) or glyoxal bisulfite adducts (JP-A-54/28 826).

It has also been proposed that the fish odor be covered using perfumed essential oils (plant extracts).

However, these processes are expensive and result in further impurities in the polymer which can adversely affect processing in the extruder or later use of the polymer.

Cleaning with hot water has also proven to be of little efficacy.

SUMMARY OF THE INVENTION

It is an object of the present invention to provide a simple process for the deodorization of used foam moldings, in particular fish crates, which enables the odor-forming impurities to be removed highly quantitatively and enables the resultant cleaned foam molding to be reused directly or at least recycled.

We have found that this object is achieved by a process in which the used foam moldings are treated a) with an aqueous solution of phosphoric acid, water-soluble primary or secondary phosphates or mixtures thereof, or b) with steam.

It is preferred according to the invention to treat the used foam moldings with an aqueous solution of phosphoric acid, water-soluble primary or secondary phosphates or mixtures thereof (variant a).

DESCRIPTION OF THE PREFERRED EMBODIMENTS

Water-soluble primary or secondary phosphates here are in particular the corresponding alkali metal salts having the formula $M^I H_2 PO_4$ and $M^I_2 HPO_4$, in which $M^I$ is an alkali metal atom such as sodium or potassium, in particular sodium.

The concentrations to be employed here depend on the degree of soiling and on the intended time for which the solution is to act on the foam moldings to be cleaned.

According to the invention, the aqueous solution preferably contains from 0.001 to 5.0% by weight, based on the solution, of phosphoric acid, water-soluble primary or secondary phosphates or mixtures thereof.

The used foam moldings employed in the process according to the invention can comprise any desired foam.

However, the process according to the invention is particularly suitable for particle foams based on styrene polymers or polyolefins.

Particular preference is given to foam moldings based on styrene polymers (polystyrene particle foam). Styrene polymers here are polystyrene or styrene copolymers containing at least 50% by weight of copolymerized styrene.

The production of these known polystyrene foam moldings and the expandable styrene polymers (EPS) on which they are based is known per se (cf., for example, EP-B-0 106 129; Kunststoffe, Volume 67 (1977), pages 617 to 621 ).

The process according to the invention can be used particularly advantageously in the deodorization of fish crates, but can also be used for the cleaning of foam moldings used for other purposes.

It has been found that the process according to the invention allows complete used fish crates to be cleaned. Surprisingly, the perfect white appearance of the originally white fish crates is restored. This is particularly important for direct recycling of the fish crates.

Fish crates which have been compressed to form briquettes or comminuted foam parts can also be cleaned in this way.

It is advantageous according to the invention for the foam moldings to be treated with water after the treatment with an aqueous solution of phosphoric acid, water-soluble primary or secondary phosphates or mixtures thereof, otherwise discoloration of the polystyrene can occur during melting, for example in the case of fish crates made from polystyrene particle foam.

EXAMPLES

Example 1

Fish crates which have been compressed to form briquettes having a density of 0.4 g/cm$^3$ were first comminuted to pieces about 2 cm$^3$ in size. 1 part by weight of these pieces was dispersed for 12 hours at room temperature in 5 parts by weight of a 0.1% strength by weight aqueous phosphoric acid solution. The aqueous phase was subsequently separated off, the pieces were redispersed in 5 parts by weight of water for 1 hour, and the water was separated off. With the aid of a press, virtually all the water was subsequently removed.

The pieces had no evident fish odor. After extrusion, ambercolored polystyrene granules with no fish odor were obtained.

If the pieces were instead dispersed for only 10 minutes in the phosphoric acid and (for subsequent washing) for 10 minutes in water, a slight fish odor was still evident.

Example 2

For work-up with the aim of re-use, an intact fish crate was sprayed with 0.1% strength by weight $Na_2HPO_4$ solution at room temperature for 12 hours.

After this treatment, the fish crate had a perfect white surface. A fish odor was no longer evident.

If the spraying was carried out for only 15 minutes with a 0.1% strength by weight $Na_2HPO_4$ solution at room temperature, the fish crate was subsequently externally clean, but a fish odor was still evident. However, if a Na$_2$HPO$_4$ solution at 60° C. was employed, the fish odor was significantly reduced.

We claim:

1. A process for removing fish odor from used foam moldings, which comprises taking used foam moldings and exposing them to
   a) an aqueous solution of phosphoric acid, water-soluble primary or secondary phosphates or mixtures thereof, which exposure results in the removal of fish odor from said used foam moldings.

2. A process as claimed in claim 1, wherein the aqueous solution contains from 0.001 to 5.0% by weight, based on the solution, of phosphoric acid, water-soluble primary or secondary phosphates or mixtures thereof.

3. A process a claimed in claim 1, wherein the foam the foam moldings comprise a polystyrene particle foam.

UNITED STATES PATENT AND TRADEMARK OFFICE
CERTIFICATE OF CORRECTION

PATENT NO.: 5,429,798

DATED: July 4, 1995

INVENTOR(S): WITT et al.

It is certified that error appears in the above-identified patent and that said Letters Patent is hereby corrected as shown below:

Column 4, claim 3, line 1, delete "the foam".

Signed and Sealed this

Fifth Day of September, 1995

Attest:

Attesting Officer

BRUCE LEHMAN

Commissioner of Patents and Trademarks